(12) United States Patent
Zhu et al.

(10) Patent No.: US 11,644,394 B2
(45) Date of Patent: May 9, 2023

(54) DEVICE AND METHOD FOR PREPARING SOLIDIFIED COHESIONLESS SOIL SPECIMEN FOR TRIAXIAL TEST

(71) Applicant: ZHEJIANG UNIVERSITY OF SCIENCE AND TECHNOLOGY, Hangzhou (CN)

(72) Inventors: Jianfeng Zhu, Hangzhou (CN); Hao Yang, Hangzhou (CN)

(73) Assignee: ZHEJIANG UNIVERSITY OF SCIENCE AND TECHNOLOGY, Hangzhou (CN)

( * ) Notice: Subject to any disclaimer, the term of this patent is extended or adjusted under 35 U.S.C. 154(b) by 0 days.

(21) Appl. No.: 17/547,424

(22) Filed: Dec. 10, 2021

(65) Prior Publication Data

US 2022/0099539 A1 Mar. 31, 2022

(30) Foreign Application Priority Data

Dec. 11, 2020 (CN) .......................... 202011464047.5
Jan. 25, 2021 (CN) .......................... 202110097891.7
Apr. 20, 2021 (CN) .......................... 202110425682.0

(51) Int. Cl.
*G01N 1/28* (2006.01)
*G01N 33/24* (2006.01)

(52) U.S. Cl.
CPC ............. *G01N 1/286* (2013.01); *G01N 33/24* (2013.01); *G01N 2203/0258* (2013.01); *G01N 2203/0284* (2013.01); *G01N 2203/0298* (2013.01)

(58) Field of Classification Search
CPC .................. G01N 1/286; G01N 33/24; G01N 2203/0258; G01N 2203/0284; G01N 2203/0298
See application file for complete search history.

(56) References Cited

U.S. PATENT DOCUMENTS

| | | | |
|---|---|---|---|
| 2018/0120283 A1* | 5/2018 | Gupta | G01N 33/24 |
| 2020/0072914 A1* | 3/2020 | Zhao | G01L 19/142 |

FOREIGN PATENT DOCUMENTS

| | | | |
|---|---|---|---|
| CN | 103335876 A | * | 10/2013 |
| CN | 209589703 U | * | 11/2019 |
| CN | 111855353 A | | 10/2020 |
| CN | 111999142 A | | 11/2020 |
| CN | 212844593 U | * | 3/2021 |

* cited by examiner

*Primary Examiner* — Ryan D Walsh

(57) ABSTRACT

A device and method for preparing a solidified cohesionless soil specimen for triaxial test. The device includes a first vessel for storing a grout, a first peristaltic pump, a grouting pipe, a first electrode rod, a direct-current power supply, a first glass stopper, a PMMA pipe, a circumferential grouting cylinder, a first hoop sleevedly provided on the circumferential grouting cylinder, a second hoop sleevedly provided on the PMMA pipe, a return pipe, a second glass stopper, a second electrode rod, a liquid outlet pipe, a first water-stop clamp, a second water-stop clamp, a second vessel for collecting an exudate, and a second peristaltic pump.

11 Claims, 9 Drawing Sheets

US 11,644,394 B2

DEVICE AND METHOD FOR PREPARING SOLIDIFIED COHESIONLESS SOIL SPECIMEN FOR TRIAXIAL TEST

CROSS-REFERENCE TO RELATED APPLICATIONS

This application claims the benefit of priority from Chinese Patent Applications No. 202011464047.5, filed on Dec. 11, 2020, No. 202110097891.7, field on Jan. 25, 2021, No. 202011579634.9, field on Dec. 28, 2020, and No. 202110425682.0, field on Apr. 20, 2021. The content of the aforementioned applications, including any intervening amendments thereto, is incorporated herein by reference in its entirety.

TECHNICAL FIELD

This application relates to geotechnical-chemical engineering, and more particularly to a device and method for preparing a solidified cohesionless soil specimen for triaxial test.

BACKGROUND

Saturated cohesionless soil, such as loose sand and silty soil, is prone to liquefaction under the action of cyclic loads such as waves and earthquakes, which will further induce engineering disasters. In view of this, a soil stabilizer has been injected into the cohesionless soil to treat the poor soil in the tunnel construction and foundation treatment. Currently, the triaxial test of the solidified cohesionless soil unit has become a primary tool for evaluating the solidification effect and exploring the mechanical properties of the solidified soil in laboratory experiments of the geotechnical engineering. During the laboratory test of triaxial mechanical properties of the solidified soil, the soil specimen is generally processed into a cylindric standard specimen with a diameter of about 39.1 mm and a height of about 80 mm (or diameter of about 38 mm and height of about 76 mm), and the solidification of the soil unit is conventionally by unidirectional grouting, which has the problem of nonuniform solidification, poor specimen integrity and difficult forming due to the exfoliation of the soil particles at the surface of the specimen. Moreover, the improper specimen-transferring method will cause damage to the specimen after grouting, which will further bring a non-negligible impact on the results of the triaxial test.

SUMMARY

In view of the defects in the prior art, an object of this application is to provide a device and method for preparing a solidified cohesionless soil specimen for the triaxial test. The device not only ensures the solidification effect of the triaxial unit through the integration of circumferential grouting, internal vertical grouting and electrochemical grouting, but also significantly attenuates the damage to the specimen when removing the specimen by means of the design of the two-piece structure.

Technical solutions of this application are described as follows.

In a first aspect, this application provides a device for preparing a solidified cohesionless soil specimen for a triaxial test, comprising:
a first vessel configured to accommodate a grout;
a first peristaltic pump;
a grouting pipe;
a first branch pipe;
a second branch pipe;
a third branch pipe;
a flow control valve;
a first electrode rod;
a direct-current (DC) power supply;
a first glass stopper;
a polymethyl methacrylate (PMMA) pipe;
a circumferential grouting cylinder;
a plurality of grouting holes;
a first hoop;
a second hoop;
a return pipe;
a second rubber tube;
a second glass stopper;
a cotton filter;
a second electrode rod;
a liquid outlet pipe;
a first rubber tube;
a first water-stop clamp;
a second water-stop clamp;
a second vessel for collecting an exudate;
a second peristaltic pump; and
a circumferential space;
wherein
the PMMA pipe has a two-piece structure; the first hoop is sleevedly provided on an outer side wall of the PMMA pipe; both ends of the PMMA pipe are open; a top opening of the PMMA pipe is provided with a first glass stopper, and a bottom opening of the PMMA pipe is provided with a second glass stopper;
the circumferential grouting cylinder has a two-piece structure; the second hoop is sleevedly provided on an outer side wall of the circumferential grouting cylinder; the plurality of grouting holes are evenly provided on a side wall of the circumferential grouting cylinder; the circumferential grouting cylinder is arranged in the PMMA pipe, and the circumferential grouting cylinder and the PMMA pipe are arranged coaxially; the first glass stopper abuts against a top end of the circumferential grouting cylinder, and the second glass stopper abuts against a bottom end of the circumferential grouting cylinder; the circumferential space is formed between the circumferential grouting cylinder and the PMMA pipe, and a soil specimen to be solidified is prepared into the solidified cohesionless soil specimen in the circumferential grouting cylinder; a first end of the grouting pipe is connected to the first vessel, and a second end of the grouting pipe is provided with the first branch pipe, the second branch pipe and the third branch pipe; the first branch pipe and the third branch pipe pass through the first glass stopper to partially extend into the circumferential space; the second branch pipe passes through the first glass stopper to be inserted into the soil specimen to be solidified in the circumferential grouting cylinder; the first peristaltic pump is arranged at the first end of the grouting pipe; the first peristaltic pump is configured to drive the grout in the first vessel to pass through the first end of the grouting pipe, and the first branch pipe and the third branch pipe at the second end of the grouting pipe in sequence to be injected into the circumferential space, and then to be injected into the soil specimen to be solidified in the circumferential grouting cylinder through the plurality of grouting holes; and the first peristaltic pump is also configured to drive the grout in the first vessel to pass through the first end of the grouting pipe, and the second branch pipe arranged at the second end of the grouting pipe in sequence to be injected into the soil specimen to be solidified in the circumferential grouting cylinder; the second electrode rod passes through the second glass stopper to be inserted into the soil specimen to be solidified; an end of the second glass stopper facing the soil specimen to be solidified is provided with the cotton filter; one end of the liquid outlet pipe passes through the second glass stopper to extend to a bottom of the cotton filter, and the other end of the liquid outlet pipe is arranged near an inlet of the second vessel; the exudate exuding from the circumferential grouting cylinder is configured to flow through the liquid outlet pipe and the inlet of the second vessel in sequence to be injected into the second vessel; one end of the return pipe extends into the circumferential space through the second glass stopper, and the other end of the return pipe is arranged near an inlet of the first vessel; the second peristaltic pump is arranged on the return pipe; the second peristaltic pump is configured to drive the grout in the circumferential space to return to the first vessel through the return pipe; one end of the first electrode rod extends into the soil specimen to be solidified in the circumferential grouting cylinder through the first glass stopper, and the other end of the first electrode rod is connected to a positive electrode of the DC power supply; an end of the second electrode rod away from the second glass stopper is connected to a negative electrode of the DC power supply; a combination of the DC power supply, the second electrode rod and the first electrode rod is configured to enable an electrochemical grouting, so as to promote a flow diffusion of the grout in the circumferential grouting cylinder;

the first peristaltic pump and the second peristaltic pump both have an adjustable output power; the first rubber tube is sleevedly provided at the end of the liquid outlet pipe arranged near the inlet of the second vessel; the first water-stop clamp is arranged on the first rubber tube; the first water-stop clamp is configured to clamp or release the first rubber tube, so as to make the first rubber tube unblocked or blocked, thereby making the liquid outlet pipe unblocked or blocked; the second rubber tube is sleevedly provided on a middle of the return pipe; the second water-stop clamp is arranged on the second rubber tube; the second water-stop clamp is configured to clamp or release the second rubber tube, so as to make the second rubber tube blocked or unblocked, thereby making the return pipe blocked or unblocked; and the flow control valve is arranged on the second branch pipe; the flow control valve is configured for controlling a flow rate of the grout in the second branch pipe, so as to achieve independent control of the flow rate of the grout in the second branch pipe.

In an embodiment, an inner diameter of the PMMA pipe is 79.1 mm; an inner diameter of the circumferential grouting cylinder is 39.1 mm or 38 mm; a diameter of each of the plurality of grouting holes is 0.075 mm, and a spacing between centers of adjacent two grouting holes is 1 mm; and a side wall of the PMMA pipe is provided with a graduation scale of a height of at least 100 mm.

In an embodiment, the flow control valve is configured to control the flow rate of the grout in the second branch pipe, such that the flow rate of the grout in the second branch pipe is less than a flow rate of the grout in the first branch pipe and the third branch pipe.

In an embodiment, the first glass stopper comprises:
a first cylinder;
a second cylinder;
a sleeve; and
a bolt;

wherein the first cylinder is larger than the second cylinder; a side wall of the second cylinder fits an inner wall of the circumferential grouting cylinder; the first cylinder and the second cylinder are coaxially connected; the second cylinder is configured to move up and down relative to the first cylinder to adjust a fitting length between the second cylinder and the circumferential grouting cylinder; the sleeve is fixedly connected to a top of the first cylinder; the bolt is penetratedly provided on the sleeve and is configured to abut against the second cylinder; the bolt is configured to be rotated to be close to or away from the second cylinder, such that the bolt abuts against the second cylinder or releases the second cylinder, thereby realizing locking and unlocking of a height of the second cylinder relative to the first cylinder; the first glass stopper is provided with a first through hole, a second through hole, a third through hole and a fourth through hole; the first branch pipe is inserted into the first glass stopper through the first through hole; the third branch pipe is inserted into the first glass stopper through the fourth through hole; the second branch pipe is inserted into the first glass stopper through the second through hole; the first electrode rod is inserted into the first glass stopper through the third through hole; an inner wall of each of the first through hole, the second through hole, the third through hole and the fourth through hole is pasted with a first anti-slip film to fix components inserted into the first glass stopper.

In an embodiment, the second glass stopper comprises a third cylinder and a fourth cylinder; the third cylinder is larger than the fourth cylinder; the third cylinder and the fourth cylinder are arranged coaxially; the cotton filter is attached to an end of the second glass stopper in contact with the soil specimen to be solidified to prevent the soil specimen to be solidified from leaking; the liquid outlet pipe and the return pipe do not pass through the cotton filter, while the second electrode rod passes through the cotton filter; the second glass stopper is provided with a fifth through hole, a sixth through hole, a seventh through hole and an eighth through hole; one end of the return pipe is arranged near the inlet of the first vessel, and the other end of the return pipe is provided with a fourth branch pipe and a fifth branch pipe; the fourth branch pipe is inserted into the second glass stopper through the fifth through hole; and the fifth branch pipe is inserted into the second glass stopper through the eighth through hole; the liquid outlet pipe passes through the second glass stopper through the sixth through hole to extend to a bottom of the cotton filter; and the second electrode rod passes through the second glass stopper through the seventh through hole to be inserted into the soil specimen to be solidified.

In an embodiment, a gauze is attached to the side wall of the circumferential grouting cylinder to prevent the soil specimen to be solidified from leaking out of the circumferential grouting cylinder.

In an embodiment, the first electrode rod, the second electrode rod and the DC power supply together establish a complete electric field inside the soil specimen to be solidified to realize the electrochemical grouting; the electric field is configured to control a flow of the grout with different charges in the soil specimen to be solidified, and is also configured to switch the positive electrode and the negative electrode of the DC power supply to change a current direction, so as to change a flow direction of the grout.

In an embodiment, the first vessel is configured to collect the grout exuded from the circumferential grouting cylinder through the liquid outlet pipe.

In an embodiment, a distance between a bottom end of the first glass stopper and a top end of the second glass stopper is 100 mm; the bottom end of the first glass stopper is aligned with a 100 mm scale line of the graduation scale on the side wall of the PMMA pipe; and the top end of the second glass stopper is aligned with a 0 mm scale line of the graduation scale on the side wall of the PMMA pipe.

In a second aspect, this application also provides a method for preparing a solidified cohesionless soil specimen using the above device, comprising:

opening the first glass stopper, and putting a soil specimen to be solidified into the circumferential grouting cylinder followed by layered compaction to form a cylindrical specimen with a diameter of 39.1 mm or 38 mm and a height of 80 mm-100 mm; and inserting the first glass stopper into the top opening of the PMMA pipe;

turning on the first peristaltic pump to drive the grout in the first vessel to be injected into the circumferential space through the first end of the grouting pipe and the first branch pipe and/or the third branch pipe at the second end of the grouting pipe in sequence; laterally injecting the grout into the soil specimen to be solidified in the circumferential grouting cylinder through the plurality of grouting holes of the circumferential grouting cylinder to perform circumferential grouting; and simultaneously driving, by the first peristaltic pump, the grout in the first vessel to pass through the first end of the grouting pipe and the second branch pipe at the second end of the grouting pipe in sequence to be injected into the soil specimen to be solidified in the circumferential grouting cylinder to perform a vertical grouting inside the soil specimen to be solidified;

after the grouting is performed for 3 hours, turning on the DC power supply to allow the DC power supply to cooperate with the second electrode rod and the first electrode rod to perform an electrochemical grouting, so as to allow the grout to flow and diffuse in the circumferential grouting cylinder until a desired solidified triaxial test specimen is obtained; wherein the grouting of the device comprises processes of grouting, standing and re-grouting; the grout is a single or mixed grout;

turning off the first peristaltic pump to stop the grouting after completing an injection of the grout, wherein during the grouting process, the second rubber tube of the return pipe is clamped by the second water-stop clamp to block the return pipe, and the first water-stop clamp is removed from the liquid outlet pipe to make the liquid outlet pipe unblocked; after the grouting is completed, the first rubber tube of the liquid outlet pipe is clamped by the first water-stop clamp to block the liquid outlet pipe, and the second water-stop clamp is removed to make the return pipe unblocked; and the second peristaltic pump is turned on to pump the grout remaining in the PMMA pipe into the first vessel through the return pipe; and after standing for a preset period of time, replacing the grout with another grout or directly repeating the above steps, to perform re-grouting.

In an embodiment, the grouting is ended through steps of:

turning on the first peristaltic pump and removing the first water-stop clamp; when the grout is blocked from being injected into the soil specimen to be solidified, and the grout fails to exude from the liquid outlet pipe due to a blockage, clamping the first rubber tube of the liquid outlet pipe with the first water-stop clamp; and turning off the first peristaltic pump to end the grouting.

Compared with the prior art, this application has the following beneficial effects.

1. Three methods are combined to enhance the solidification of the soil element.

(1) The vertical grouting pipe is inserted into the specimen to perform vertical grouting, so as to allow the grout to flow from the inside to the outside.

(2) The grout in the circumferential space laterally penetrates into the specimen through the plurality of grouting holes on the circumferential grouting cylinder, and under the continuous pressure provided by the peristaltic pump the solidification effect is strengthened by combining the characteristic that the transverse permeability coefficient of the soil is greater than the vertical permeability coefficient.

(3) The electrochemical grouting further promotes the diffusion of the grout, and the drive of the electric field effectively avoids the problem that the grout fails to infiltrate into the small pores.

2. The PMMA pipe and the circumferential grouting cylinder both have a two-piece structure. After the solidification treatment is completed, the specimen can be removed under an interference-free condition. Therefore, the device provided herein can keep the specimen always under a highly interference-free condition during the processes of loading, grouting, and collection.

3. The independent design of the return pipe and the liquid outlet pipe realizes the recycling of the uncontaminated grout and the reasonable treatment of the exudate from the specimen.

Figure 1:
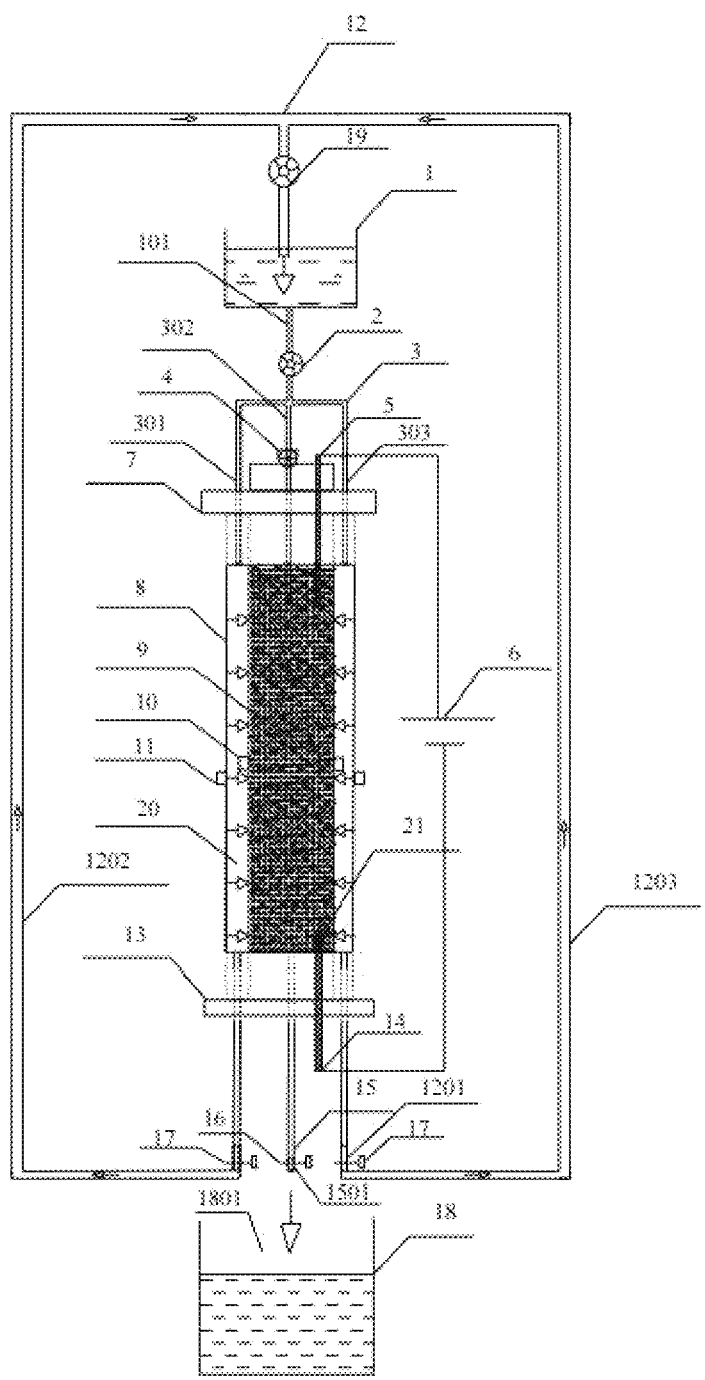
FIG. 1 schematically shows a device for preparing a solidified cohesionless soil specimen for the triaxial test according to an embodiment of this application.

In the drawings, 1: first vessel; 101: inlet of the first vessel; 2: first peristaltic pump; 3: grouting pipe; 301: first branch pipe; 302: second branch pipe; 303: third branch pipe; 4: flow control valve; 5: first electrode rod; 6: direct-current (DC) power supply; 7: first glass stopper; 701: first cylinder; 7011: first lateral convex disc; 702: second cylinder; 7021: second lateral convex disc; 703: sleeve; 704: bolt; 705: first through hole; 706 second through hole; 707: third through hole; 708: fourth through hole; 709: first anti-slip film; 8: PMMA pipe; 801: graduation scale; 802: first half pipe; 803: second half pipe; 9: circumferential grouting cylinder; 901: grouting hole; 902: third half pipe; 903: fourth half pipe; 10: second hoop; 11: first hoop; 12: return pipe; 1201: second rubber tube; 1202: fourth branch pipe; 1203: fifth branch pipe; 13: second glass stopper; 1301: third cylinder; 13011: third lateral convex disc; 1302: fourth cylinder; 1303: fifth through hole; 1304: sixth through hole; 1305: seventh through hole; 1306: eighth through hole; 1307: cotton filter; 1308: second anti-slip film; 14: second electrode rod; 15: liquid outlet pipe; 1501: first rubber tube; 16: first water-stop clamp; 17: second water-stop clamp; 18: second vessel; 1801: inlet of the second vessel; 19: second peristaltic pump; 20: circumferential space; and 21: gauze.

DETAILED DESCRIPTION OF EMBODIMENTS

This application will be described in detail below with reference to the embodiments and accompany drawings.

Figure 2:
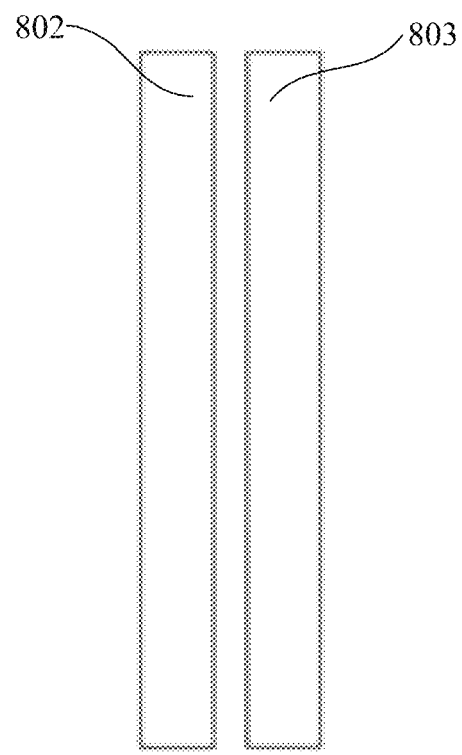
FIG. 2 is a side view of a PMMA pipe according to an embodiment of this application.
Figure 3:
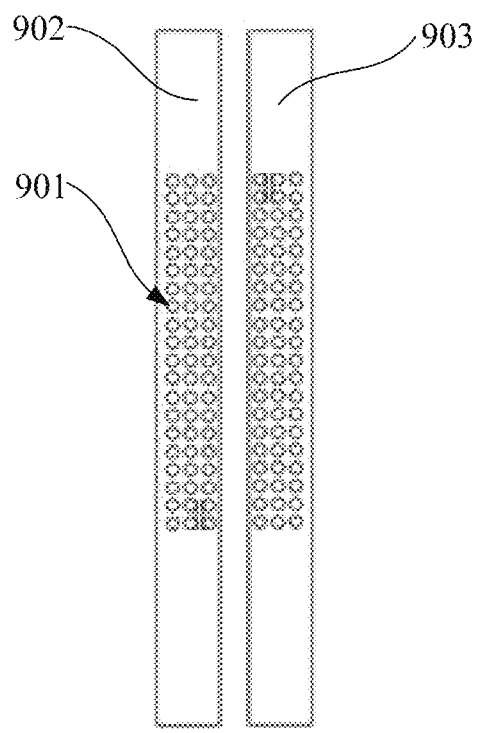
FIG. 3 is a side view of a circumferential grouting cylinder according to an embodiment of this application.

As shown in FIGS. 1-3, this application provides a device for preparing a solidified cohesionless soil specimen for the triaxial test, including a first vessel 1, a first peristaltic pump 2, a grouting pipe 3, a first branch pipe 301, a second branch pipe 302, a third branch pipe 303, a flow control valve 4, a first electrode rod 5, a DC power supply 6, a first glass stopper 7, a PMMA pipe 8, a circumferential grouting cylinder 9, a plurality of grouting holes 901; a second hoop 10, a first hoop 11, a return pipe 12, a second rubber tube 1201, a second glass stopper 13, a cotton filter 1307; a second electrode rod 14, a liquid outlet pipe 15, a first rubber tube 1501, a first water-stop clamp 16, a second water-stop clamp 17, a second vessel 18, a second peristaltic pump 19, and a circumferential space 20.

The first vessel 1 is configured to accommodate a grout.

The PMMA pipe 8 has a two-piece structure. The first hoop 11 is sleevedly provided on an outer side wall of the PMMA pipe 8. Both of two ends of the PMMA pipe 8 are open. A top opening of the PMMA pipe is provided with a first glass stopper 7, and a bottom opening of the PMMA pipe is provided with a second glass stopper 13. In this embodiment, the PMMA pipe 8 includes a first half pipe 802 and a second half pipe 803, which are separated. The first half pipe 802 and the second half pipe 803 are buckled together to form a PMMA pipe 8 in a structure of two-piece. The first hoop 11 is sleevedly provided on the outer side wall of each of the first half pipe 802 and the second half pipe 803, allowing the first half pipe 802 and the second half pipe 803 to be fixed to form a complete PMMA pipe 8.

Referring to FIGS. 1, 3, 5, and 12, the circumferential grouting cylinder 9 has the two-piece structure. The second hoop 10 is sleevedly provided on an outer side wall of the circumferential grouting cylinder 9. The plurality of grouting holes 901 are provided on a side wall of the circumferential grouting cylinder 9. The circumferential grouting cylinder 9 is arranged in the PMMA pipe 8, and the circumferential grouting cylinder 9 and the PMMA pipe 8 are arranged coaxially. The first glass stopper 7 abuts against a top end of the circumferential grouting cylinder 9, and the second glass stopper 13 abuts against a bottom end of the circumferential grouting cylinder 9. The circumferential space 20 is formed between the circumferential grouting cylinder 9 and the PMMA pipe 8, and a soil specimen to be solidified is prepared into the solidified cohesionless soil specimen in the circumferential grouting cylinder 9. A first end of the grouting pipe 3 is connected to the first vessel 1, and a second end of the grouting pipe 3 is provided with the first branch pipe 301, the second branch pipe 302 and the third branch pipe 303. The first branch 301 pipe and the third branch pipe 303 pass through the first glass stopper 7 to partially extend into the circumferential space 20. The second branch pipe 302 passes through the first glass stopper 7 to be inserted into the soil specimen to be solidified in the circumferential grouting cylinder 9. The first peristaltic pump 2 is arranged at the first end of the grouting pipe 3. The first peristaltic pump 2 is configured to drive the grout in the first vessel 1 to pass through the first end of the grouting pipe 3, and the first branch pipe 301 and the third branch pipe 303 at the second end of the grouting pipe 3 in sequence to be injected into the circumferential space 20, and then to be injected into the soil specimen to be solidified in the circumferential grouting cylinder 9 through the plurality of grouting holes 901. And the first peristaltic pump 2 is also configured to drive the grout in the first vessel 1 to pass through the first end of the grouting pipe 3 and the second branch pipe 302 arranged at the second of the grouting pipe 3 in sequence to be injected into the soil specimen to be solidified in the circumferential grouting cylinder 9. The second electrode rod 14 passes through the second glass stopper 13 to be inserted into the soil to be solidified. An end of the second glass stopper 13 facing the soil specimen to be solidified is provided with the cotton filter 1307. One end of the liquid outlet pipe 15 passes through the second glass stopper 13 to extend to a bottom of the cotton filter 1307, and the other end of the liquid outlet pipe 15 is arranged near an inlet 1801 of the second vessel 18. The exudate exuding from the circumferential grouting cylinder 9 is configured to flow through the liquid outlet pipe 15 and the inlet 1801 in sequence to be injected into the second vessel 18. One end of the return pipe 12 extends into the circumferential space 20 through the second glass stopper 13, and the other end of the return pipe 12 is arranged near an inlet 101 of the first vessel 1. The second peristaltic pump 19 is arranged on the return pipe 12. The second peristaltic pump 19 is configured to drive the grout in the circumferential space 20 to return to the first vessel 1 through the return pipe 12. One end of the first electrode rod 5 extends into the soil specimen to be solidified in the circumferential grouting cylinder 9 through the first glass stopper 7, and the other end of the first electrode rod 5 is connected to a positive electrode of a DC power supply 6. An end of the second electrode rod 14 away from the second glass stopper 13 is connected to a negative electrode of the DC power supply 6. A combination of the DC power supply 6, the second electrode rod 14, and the first electrode rod 5 is configured to enable an electrochemical grouting, so as to promote a flow diffusion of the grout in the circumferential grouting cylinder 9.

In this embodiment, the circumferential grouting cylinder 9 includes a third half pipe 902 and a fourth half pipe 903, which are separated from each other. The third half pipe 902 and the fourth half pipe 903 can be buckled together to form the circumferential grouting cylinder 9 in a structure of two-piece. The second hoop 10 is sleevedly provided on the outer side wall of each of the combined third half pipe 902 and the fourth half pipe 903, allowing the third half pipe 902 and the fourth half pipe 903 to be fixed to form a complete circumferential grouting cylinder 9.

In this embodiment, the plurality of grouting holes 901 are evenly provided on a side wall of the circumferential grouting cylinder 9 along the circumference of the circumferential grouting cylinder 9, so that the grout in the circumferential space 20 passes through the plurality of grouting holes 901 along the circumferential direction of the circumferential grouting cylinder 9 to be laterally penetrated into the soil specimen to be solidified. In this embodiment, the plurality of grouting holes 901 are evenly arranged on the side wall of each of the third half pipe 902 and the fourth half pipe 903. In this embodiment, the soil is compacted in layers in the circumferential grouting cylinder 9 to form a soil specimen to be solidified, by means of the methods including static pressure and compaction. The excess grout returns to the first vessel 1 to be reused through the return pipe 12, improving the utilization rate of the grout. The second vessel 18 is configured to collect the grout exudated from the circumferential grouting cylinder 9 through the liquid outlet pipe 15, and the arrangement of second vessel 18 prevents the grout exudated from the liquid outlet pipe 15 from being discharged randomly, causing the pollution of the environment. In this embodiment, the first peristaltic pump 2 is configured to drive the grout in the first vessel 1 to be injected into the circumferential space 20 through the first end of the grouting pipe 3 and the first branch pipe 301 and the third branch pipe 303 arranged at the second end of the grouting pipe 3 in sequence. The liquid outlet pipe 15 is arranged above the inlet 1801 or extends into the second vessel 18. In addition, the first electrode rod 5, the second electrode rod 14 and the DC power supply 6 together establish a complete electric field inside the soil specimen to be solidified to realize the electrochemical grouting. The electric field is configured to control a flow of the grout with different charges in the soil specimen to be solidified, and is configured to switch the positive electrode and the negative electrode of the DC power supply 6 to change a current direction, so as to change a flow direction of the grout. In some embodiments, during the electrochemical grouting, the direction of the current changes at a preset interval, so that the flow direction of the grout is adjusted, such that the grout further diffuses uniformly, until the desired solidified triaxial test specimen is obtained. The preset time can be but not limited to one hour.

Referring to FIG. 1, the first peristaltic pump 2 and the second peristaltic pump 19 both have an adjustable output power. The first rubber tube 1501 is sleevely provided at the end of the liquid outlet pipe 15 arranged near the inlet 1801 of the second vessel 18. The first water-stop clamp 16 is arranged on the first rubber tube 1501. The first water-stop clamp 16 is configured to clamp or release the first rubber tube 1501, so as to make the first rubber tube 1501 unblocked or blocked, thereby making the liquid outlet pipe 15 unblocked or blocked. The second rubber tube 1201 is sleevely provided on a middle of the return pipe 17. The second water-stop clamp 17 is arranged on the second rubber tube 1201. The second water-stop clamp 17 is configured to clamp or release the second rubber tube 1201, so as to make the second rubber tube 1201 blocked or unblocked, thereby making the return pipe 12 blocked or unblocked. In this embodiment, the first peristaltic pump 2 has an adjustable output power, such that the flow rate of the grout in the grouting pipe 3 is adjusted, and the second peristaltic pump 19 is adjusted, such that the flow rate of the grout in the return pipe 12 is adjusted.

In this embodiment, the first water-stop clamp 16 is arranged on the first rubber tube 1501 of the outlet pipe 15. The first rubber tube 1501 is clamped to control whether the grout in the liquid outlet pipe 15 flows out. The second water-stop clamp 17 is arranged on the second rubber tube 1201 of the return pipe 12, and is configured to clamp the second rubber tube 1201 of the return pipe 17 during the grouting process. After the grouting is completed, the second water-stop clamp 17 is removed and the second peristaltic pump 19 is turned on to recycle the remaining grout into the first vessel 1.

During the grouting process, the first water-stop clamp 16 is removed. When no exudated grout flows out, and the grout is blocked from being injected due to the blockage of the grouting ends. The first water-stop clamp 16 clamps the first rubber tube 1501 at a rear end of the liquid outlet pipe 15, the second water-stop clamp 17 is removed, and the second peristaltic pump 19 is turned on to recycle the excess grout into the first vessel 1 to prepare for reusing it.

Referring to FIG. 1, the flow control valve 4 is arranged on the second branch pipe 302. The flow control valve 4 is configured to control the flow rate of the grout in the second branch pipe 302, such that the flow rate of the grout in the second branch pipe 302 is less than a flow rate of the grout in the first branch pipe 301 and the third branch pipe 303.so as to prevent the flow rate of the vertical grouting through the second branch pipe 302 from being synchronized with that of the circumferential grouting through the first branch pipe 301 or the third branch pipe 303, thereby preventing the flow rate of the grout in the second branch pipe 302 from being too high to facilitate the solidification inside the specimen. In this embodiment, the flow control valve 4 is configured to control the flow rate of the grout in the second branch pipe 302, such that the flow rate of the grout in the second branch pipe 302 is less than a flow rate of the grout in the first branch pipe 301 and the third branch pipe 303.

Figure 4:
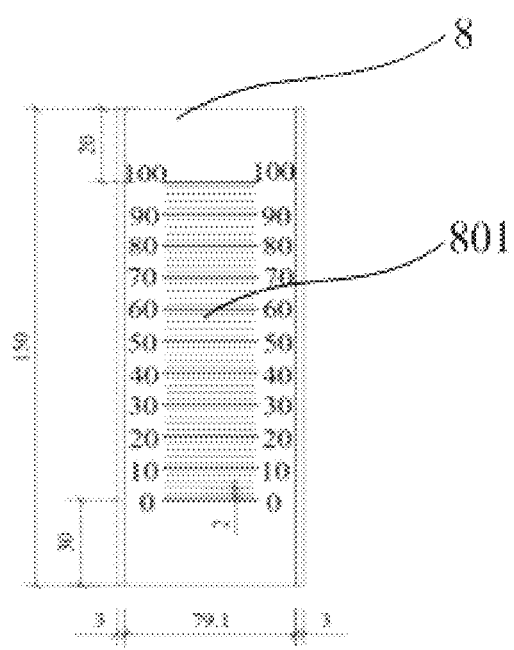
FIG. 4 is a front view of the PMMA pipe (unit: mm) according to an embodiment of this application.
Figure 5:
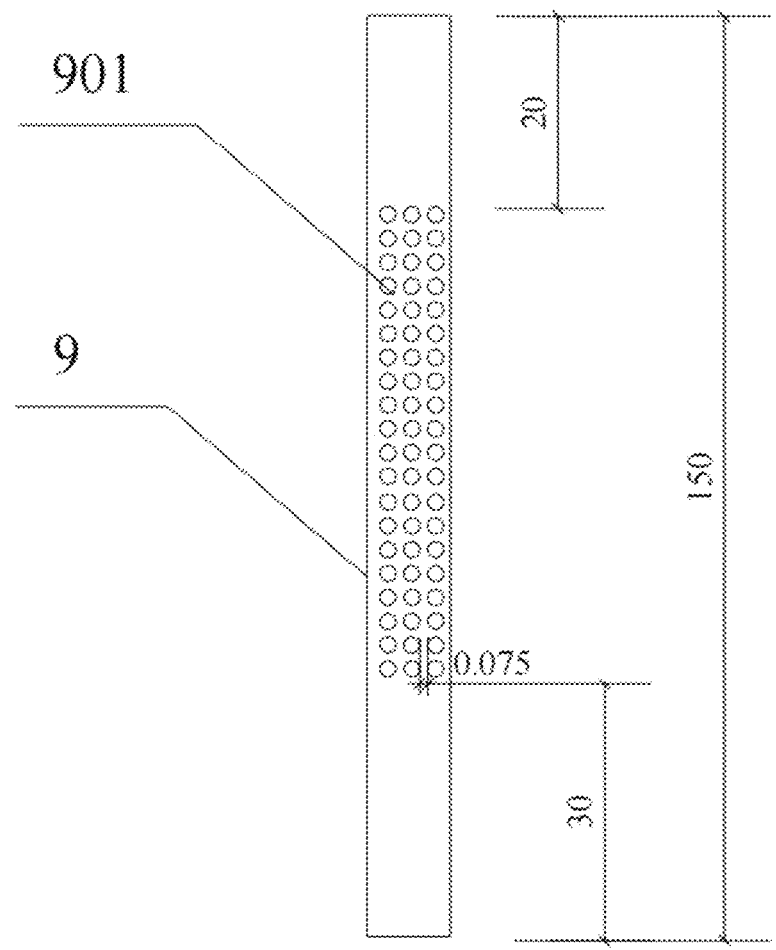
FIG. 5 is a front view of the circumferential grouting cylinder (unit: mm) according to an embodiment of this application.

In this embodiment, as shown in FIGS. 2 and 4, the second hoop is sleevely provided on the outer side wall of the circumferential grouting cylinder in a structure of two-piece to fix the circumferential grouting cylinder into a cylinder, and fix the top and bottom ends of the circumferential grouting cylinder 9 by the circular slots of the first glass stopper 7 and the second glass stopper 13.

Referring to FIG. 4, an inner diameter of the PMMA pipe 8 is 79.1 mm. An inner diameter of the circumferential grouting cylinder is 39.1 mm or 38 mm. A diameter of each of the plurality of grouting holes 901 is 0.075 mm, and a spacing between centers of adjacent two grouting holes 901 is 1 mm. The side wall of PMMA pipe 8 is provided with a graduation scale 801 ruler of a height of at least 100 mm. In this embodiment, the arrangement of the graduation scale 801 is conducive to compacting in layers when preparing the soil specimen to be solidified, and ensuring the precise production of the soil specimen to be solidified for the triaxial test. And the circumferential grouting cylinder 9 is made of PMMA with a thickness of 1 mm. In this embodiment, the graduation scale is arranged on the side wall of the first half pipe 802 and/or the second half pipe 803.

In this embodiment, the inner diameter of the PMMA pipe 8 is 79.1 mm, the height is 150 mm, and the thickness of the wall is 3 mm. As shown in FIG. 4, the graduation scale includes a main scale line and a minor scale line. The distance between adjacent main scale lines is 10 mm, and the distance between adjacent minor scale lines is 2 mm. The arrangement of the main scale line and the minor scale line is conducive to the layered compaction and meeting the requirement of the specific size for the soil specimen to be solidified. The upper edge of the graduation scale 801 is an upper limit of the scale line (at 100 mm of the graduation scale 801), and the lower edge of the graduation scale 801 is the lower limit of the scale line (at 0 mm of the graduation scale 801). A distance between the top end of the PMMA pipe 8 and the upper limit of the scale line is 20 mm, and a distance between the bottom end of the PMMA pipe 8 and the lower limit of the scale line is 30 mm. The part of the PMMA pipe 8 without the graduation scale 801 is used to install the first glass stopper 7 and the second glass stopper 13. The height of the soil specimen to be solidified is ensured to be within 80 mm-100 mm by the graduation scale 801 on the side wall of the PMMA pipe 8 and a first glass stopper 7, which is adjusted in height.

Referring to FIG. 1, a gauze 21 is attached to the side wall of the circumferential grouting cylinder 9 to prevent the soil specimen to be solidified from leaking out of the circumferential grouting cylinder 9.

In this embodiment, the top end of the second glass stopper 13 is aligned with the 0 mm scale line of the graduation scale 801 on the side wall of the PMMA pipe 8. Considering that the height of the first glass stopper 7 is adjusted, a bottom end of the first glass stopper 7 can be aligned with different scale lines of the graduation scale 801 on the side wall of the PMMA pipe 8. In this embodiment, the bottom end of the first glass stopper 7 can be aligned with scale lines within 80 mm-100 mm of the graduation scale 801.

Referring to FIGS. 6-9, the first glass stopper 7 includes a first cylinder 701, a second cylinder 702, a sleeve 703, and a bolt 704. The first cylinder is larger than the second cylinder. A side wall of the second cylinder 702 fits an inner wall of the circumferential grouting cylinder 9. The first cylinder 701 and the second cylinder 702 are coaxially connected. The second cylinder 702 is configured to move up and down relative to the first cylinder 701 to adjust a fitting length between the second cylinder 702 and the circumferential grouting cylinder 9. The sleeve 703 is arranged where the first cylinder 701 is connected with the second cylinder 702. The bolt 704 is penetratedly provided on the sleeve 703 and is configured to abut against the second cylinder 702. The bolt 704 is configured to be rotated to be close to or away from the second cylinder 702, such that the bolt 704 abuts against the second cylinder 702 or releases the second cylinder 702, thereby realizing locking and unlocking of a height of the second cylinder 702 relative to the first cylinder 701. The first glass stopper 7 is provided with a first through hole 705, a second through hole 706, a third through hole 707, and a fourth through hole 708. The first branch pipe 301 is inserted into the first glass stopper 7 through the first through hole 705, and the third branch pipe 303 is inserted into the first glass stopper 7 through the fourth through hole 708. The second branch pipe 302 is inserted into the first glass stopper 7 through the second through hole 706. The first electrode rod 5 is inserted into the first glass stopper 7 through the third through hole 707. An inner wall of each of the first through hole 705, the second through hole 706, the third through hole 707 and the fourth through hole 708 is pasted with a first anti-slip film 709 to fix components inserted into the first glass stopper 7. In this embodiment, the height of the second cylinder 702 relative to the first cylinder 701 is adjusted, so that the height of the specimen can be adjusted by the first glass stopper 7, allowing for a broadened application range.

Figure 9:
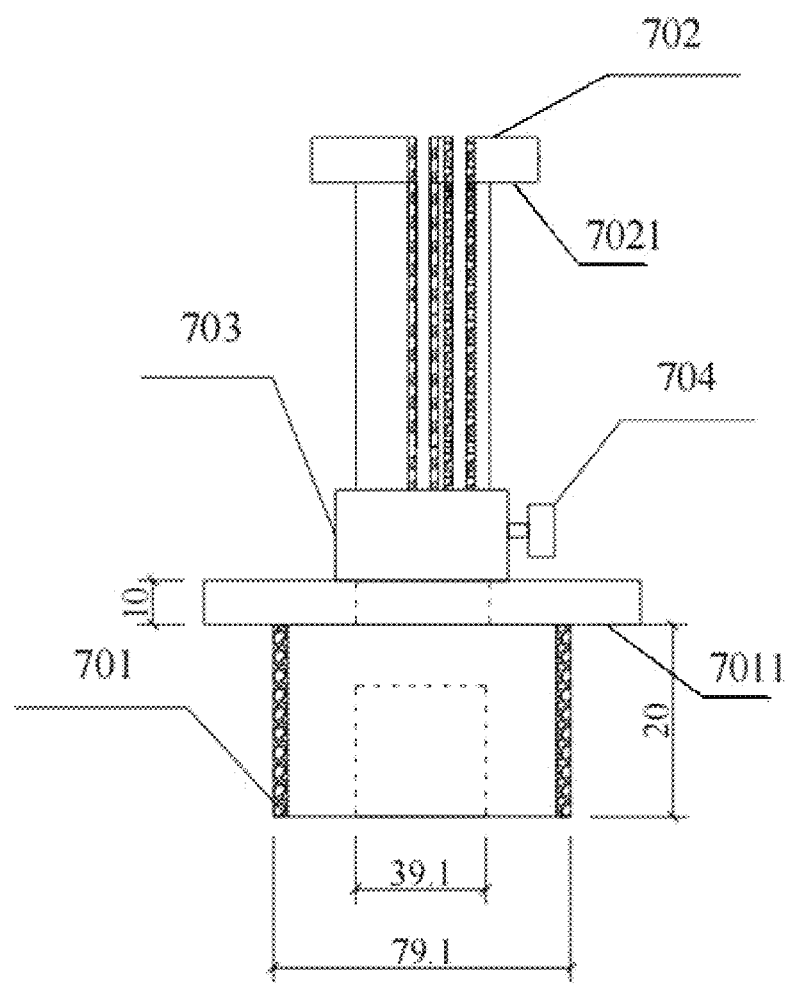
FIG. 9 is a side view of the first glass stopper (unit: mm) according to an embodiment of this application.
Figure 10:
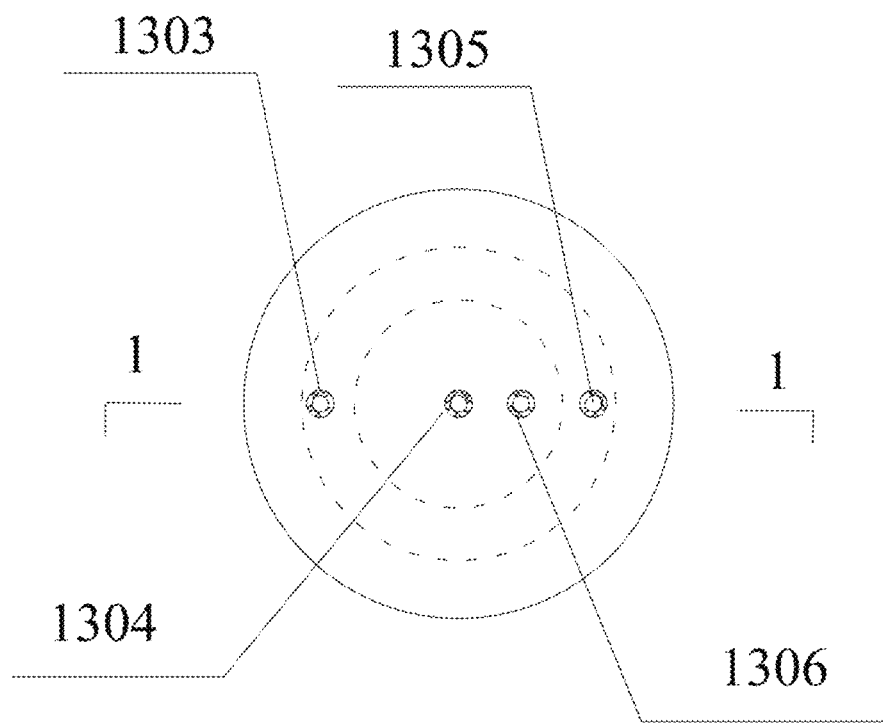
FIG. 10 is a top view of a second glass stopper (unit: mm) according to an embodiment of this application.

Referring to an embodiment shown in FIG. 9, a top of the first cylinder 701 is provided with a first lateral convex disc 7011, which is in contact and fits the top of the PMMA pipe 8 to realize the fixation of the first cylinder 701 relative to the PMMA pipe 8. The top of the second cylinder 702 is provided with a second lateral convex disc 7021, which is used to be in contact and fit the top of the sleeve 703, to limit the height of the second cylinder 702 relative to the first cylinder 701, so that a minimum height of the specimen is 80 mm. In this embodiment, the first lateral convex disc 7011 and the first cylinder 701 are unibody, thereby the outer diameter of the top of the first cylinder 701 becomes larger, and the position of the first cylinder 701 is restricted, when the first lateral convex disc 7011 abuts against the top of the PMMA pipe 8. The second lateral convex disc 7011 and the second cylinder 702 are unibody, thereby the outer diameter of the top of the second cylinder 702 becomes larger, and the position of the second cylinder 702 is restricted, such that the second cylinder 702 fails to move downward relative to the first cylinder 701, when the bottom of the second lateral convex disc 7021 abuts against the top of the sleeve 703.

Referring to FIGS. 10-13, the second glass stopper 13 includes a third cylinder 1301 and a fourth cylinder 1302. The third cylinder is larger than the fourth cylinder; the third cylinder. The third cylinder 1301 and the fourth cylinder 1302 are arranged coaxially. The cotton filter 1307 is attached to an end of the second glass stopper 13 in contact with the soil specimen to be solidified to prevent the soil specimen to be solidified from leaking. The liquid outlet pipe 15 do not pass through the cotton filter 1307, while the second electrode rod 14 and the return pipe pass through the cotton filter 1307. The second glass stopper 13 is provided with a fifth through hole 1303, a sixth through hole 1304, a seventh through hole 1305 and an eighth through hole 1306. One end of the return pipe 12 is arranged near the inlet 101, and the other end of the return pipe 12 is provided with a fourth branch pipe 1202 and a fifth branch pipe 1203. The fourth branch pipe 1202 is inserted into the second glass stopper 13 through the fifth through hole 1303, and the fifth branch pipe 1203 is inserted into the second glass stopper 13 through the eighth through hole 1306. The liquid outlet pipe 15 passes through the second glass stopper 13 through the sixth through hole 1304 to extend to the bottom of the cotton filter 1307. The second electrode rod 14 passes through the second glass stopper 13 through the seventh through hole 1305 to be inserted into the soil specimen to be solidified. In this embodiment, the middle of each of the fourth branch pipe 1202 and the fifth branch pipe 1203 is sleevedly provided with the second rubber tube 1201. Each of two second rubber tubes 1201 is provided with the second water-stop clamp 17. Each of two second water-stop clamps 17 is configured to clamp or release the corresponding second rubber tube 1201, so as to make the fourth branch pipe 1202 and/or the fifth branch pipe 1203 blocked or unblocked.

In this embodiment, the bottom of the third cylinder 1301 is provided with a third lateral convex disc 13011, which is in contact and fits the bottom of the PMMA pipe 8 to realize the fixation of the third cylinder 1301 relative to the PMMA pipe 8. In this embodiment, the third lateral convex disc 13011 and the third cylinder 1301 are unibody, thereby the outer diameter of the bottom of the third cylinder 1301 becomes larger, and the position of the third cylinder 1301 is restricted, when the top of the third lateral convex disc 13011 abuts against the bottom of the PMMA pipe 8.

Figure 6:
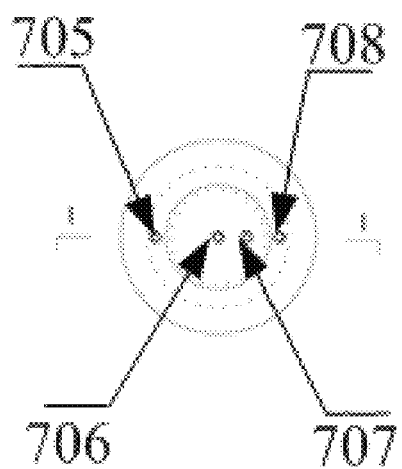
FIG. 6 is a top view of a first glass stopper (unit: mm) according to an embodiment of this application.
Figure 7:
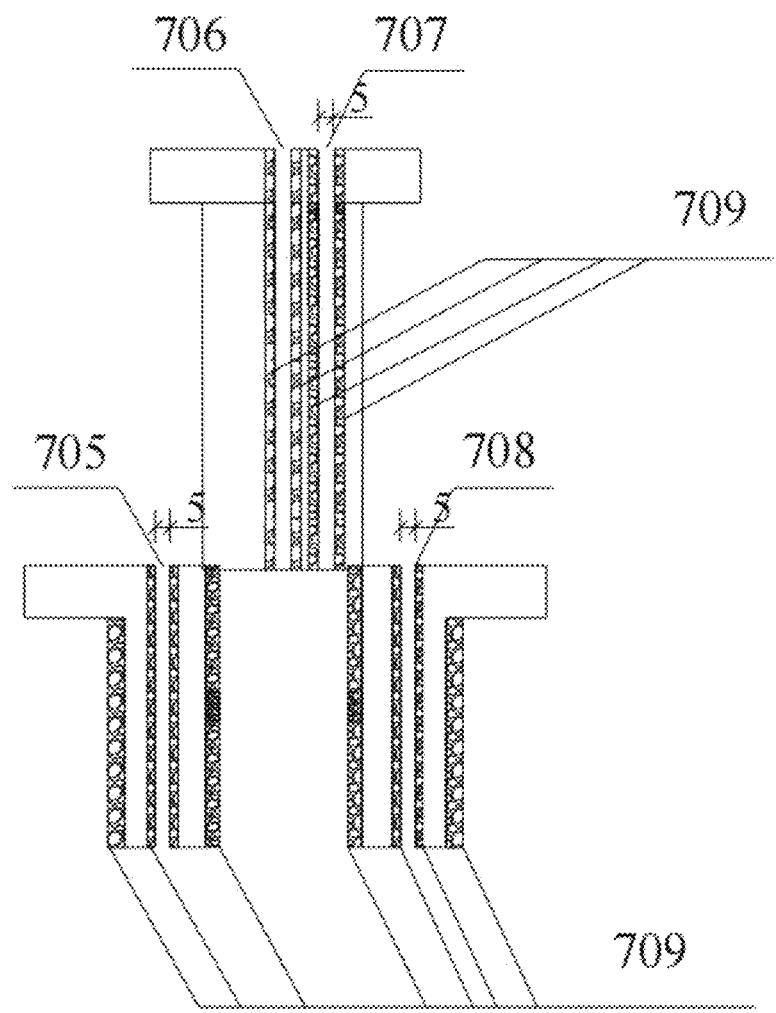
FIG. 7 is a cross-sectional view of the first glass stopper in FIG. 6.
Figure 8:
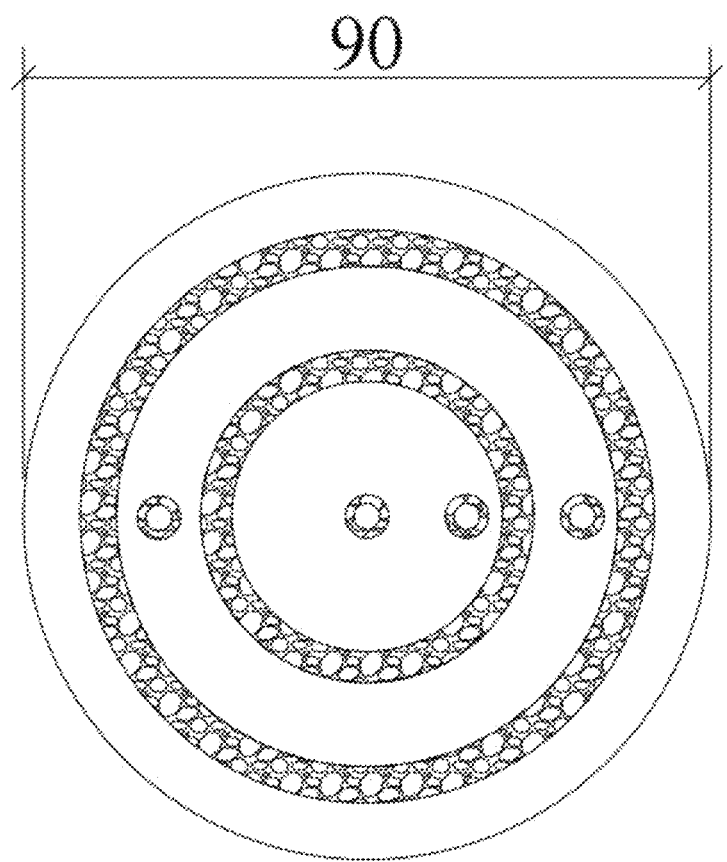
FIG. 8 is a bottom view of the first glass stopper (unit: mm) according to an embodiment of this application.

In an embodiment, the first glass stopper 7 is a cylinder with a diameter of 95 mm and a height of 30 mm. The first through hole 705 and the fourth through hole 708 are circular holes with a diameter of 5 mm symmetrically distributed on both sides of the center of the first glass stopper 7. A distance between the center of a through hole 705 and the center of the fourth through hole 708 is 30 mm. As shown in FIG. 6, the grouting pipe 3 with an inner diameter of 3 mm and an outer diameter of 9 mm is inserted into a 5 mm circular hole, the first anti-slip film 709 on the hole wall of the glass stopper 7 is elastic. Using the elasticity of the first anti-slip film 709 of the first glass stopper 7, the 5 mm holes can make the first glass stopper 7 closely fit the outer wall with an outer diameter of 9 mm of the grouting pipe 3, such that a position of the grouting pipe 3 is strictly fixed to prevent the leakage of the grout. An end of the first glass stopper 7 is provided with a circular slot with a depth of 20 mm. The circular slot has the same horizontal cross-sectional shape as the circumferential grouting cylinder 9. When the first glass stopper 7 is fixedly connected to the circumferential grouting cylinder 9, the outer wall of the second cylinder 702 fits the inner wall of the circumferential grouting cylinder 9, and the second cylinder 702 moves downward relative to the first cylinder 701 to make the fitting length between the second cylinder 702 and the circumferential grouting cylinder 9 longer, to make the bottom of the second cylinder 702 reach to the scale line at the required height. The position of the second cylinder 702 is fixed relative to the first cylinder 701 by the bolt 704, such that the fitting length between the second cylinder 702 and the circumferential grouting cylinder is unchanged, thereby ensuring the height of the specimen unchanged.

Figure 11:
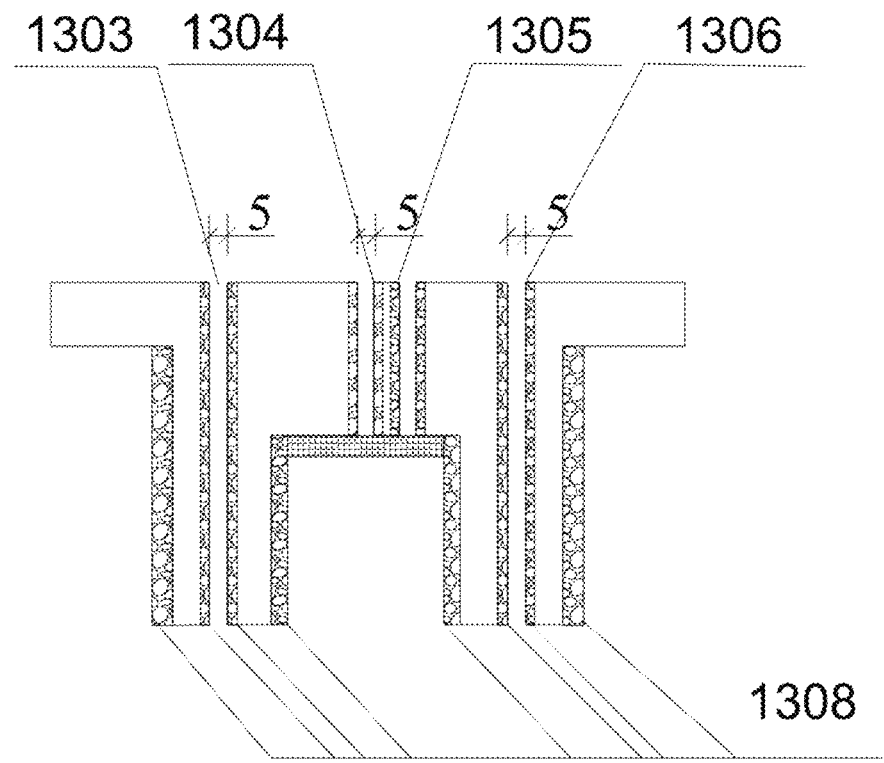
FIG. 11 is a cross-sectional view of the second glass stopper in FIG. 10.
Figure 12:
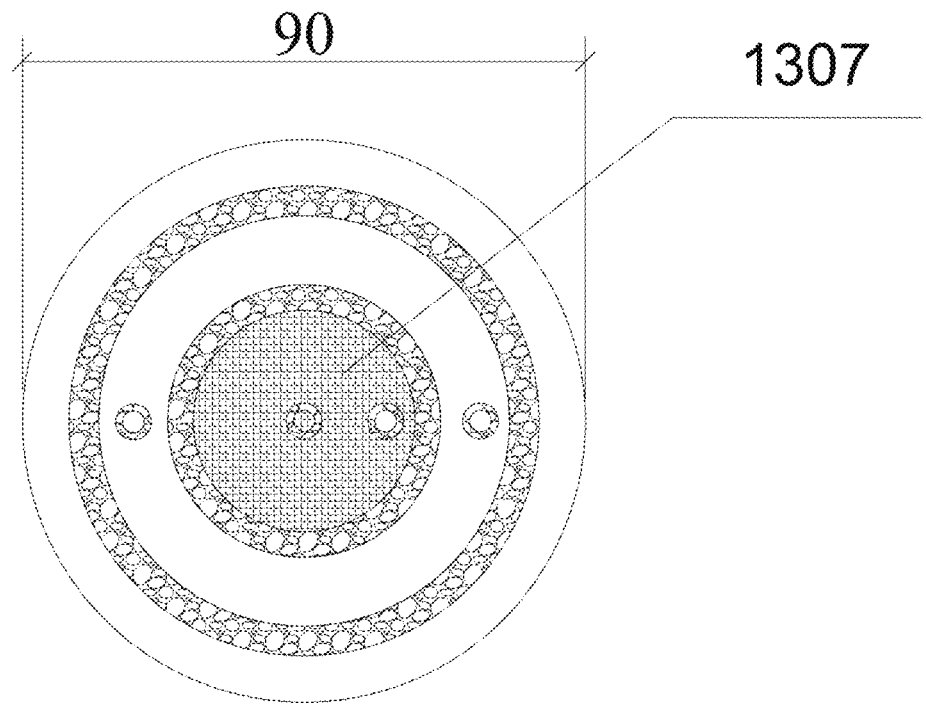
FIG. 12 is a bottom view of the second glass stopper (unit: mm) according to an embodiment of this application.
Figure 13:
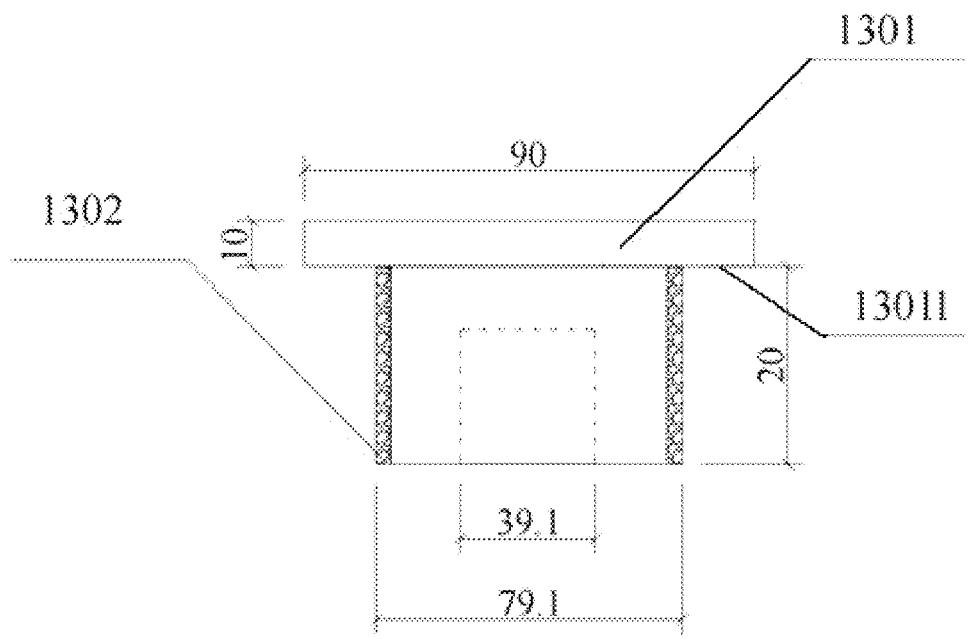
FIG. 13 is a side view of the second glass stopper (unit: mm) according to an embodiment of this application.

Referring to FIGS. 1, 11, and 12, the cotton filter 1307 is attached to a top end of the second glass stopper 13 in contact with the soil specimen to be solidified to prevent the soil specimen to be solidified from leaking. The liquid outlet pipe 15 do not pass through the cotton filter 1307, while the second electrode rod 14 and the return pipe 12 passes through the cotton filter 1307. The sixth through hole 1304 is located at the center of the bottom surface of the second glass stopper 13, the fifth through hole 1303 and the eighth through hole 1306 are symmetrically distributed on both sides of the center of the second glass stopper 13, and a clear distance between the center of the second glass stopper 13 and the edge of the fifth through hole 1303 and a clear distance between the center of the second glass stopper 13 and the edge of the eighth through hole 1306 are both 30 mm. The eighth through hole 1305 is distributed in the area where the second glass stopper 13 is in contact with the specimen. The hole diameter of each of the fifth through hole 1303, the sixth through hole 1304, the seventh through hole 1305, and the eighth through hole 1306 is 5 mm, and the inner wall of each of them is pasted with a second anti-slip film 1308. The components connected in the fifth through hole 1303, the sixth through hole 1304, the seventh through hole 1305 and the eighth through hole 1306 all have an outer diameter of 4.5 mm. The inner diameter of each of the grouting pipe 3, the liquid outlet pipe 15, and the return pipe 12 is 2 mm.

Referring to FIG. 1, a method for preparing the solidified cohesionless soil specimen for the triaxial test using the above device is illustrated, which includes the following steps.

The first glass stopper 7 is opened, and the soil specimen to be solidified is put into the circumferential grouting cylinder 9 followed by layered compaction to form a cylindrical specimen with a diameter of 39.1 mm or 38 mm and a height of 80 mm-100 mm; and the first glass stopper 7 is inserted into the top opening of the PMMA pipe 8, to adjust the bolt 704 to make the bottom of the first glass stopper 7 reach the top of the specimen.

The first peristaltic pump 2 is turned on to drive the grout in the first vessel 1 to be injected into the circumferential space 20 through the first end of the grouting pipe 3 and the first branch pipe 301 and/or the third branch pipe 303 at the second end of the grouting pipe 3 in sequence. The grout is laterally injected into the soil specimen to be solidified in the circumferential grouting cylinder 9 through the plurality of grouting holes 901 of the circumferential grouting cylinder 9 to perform the circumferential grouting. And the grout in the first vessel 1 is simultaneously driven by the first peristaltic pump 2 to pass through the first end of the grouting pipe 3 and the second branch pipe 302 at the second end of the grouting pipe 3 in sequence to be injected into the soil specimen to be solidified in the circumferential grouting cylinder 9 to perform a vertical grouting inside the soil specimen to be solidified.

After the grouting is performed for 3 hours, the DC power supply 6 is turned on, the DC power supply 6, to cooperate with the second electrode rod 14 and the first electrode rod 5 to perform the electrochemical grouting, so as to allow the grout flow and diffuse in the soil specimen to be solidified until a desired solidified triaxial test specimen is obtained.

The grouting of the device includes processes of grouting, standing and re-grouting. The grout is a single or mixed grout; The first peristaltic pump 2 is turned off to stop the grouting after completing an injection of the grout, in which during the grouting process, the second rubber tube 1201 of the return pipe 12 is clamped by the second water-stop clamp 17 to block the return pipe 12, and the first water-stop clamp 16 is removed from the liquid outlet pipe 15 to make the liquid outlet pipe 15 unblocked. After the grouting is completed, the first rubber tube 1501 of the liquid outlet pipe 15 is clamped by the first water-stop clamp 16 to block the liquid outlet pipe 15, and the second water-stop clamp 17 is removed to make the return pipe 12 unblocked. And the second peristaltic pump 12 is turned on to pump the grout remaining in the PMMA pipe into the first vessel 1 through the return pipe 12.

After standing for a preset period of time, the grout is replaced with another grout or directly repeating the above steps, to perform re-grouting.

The device for preparing the specimen is suitable for a variety of grouting methods including a single grouting, multi-step grouting, and timing cyclic grouting. During the single grouting, the injection of the grouting completes at one time. During the multi-step grouting, the grout has many kinds. The single grouting can only inject one kind of the grout, and can perform the injection of another kind of grout, after standing, until the injection of all of the grout is completed. During the timing cyclic grouting, a cycle of injection is performed every preset time, in which the injection of all the grout at one time is called a cycle.

The grouting is ended through the following steps.

The first peristaltic pump 2 is turned on and the first water-stop clamp 16 is removed, when the grout is blocked from being injected into the soil specimen to be solidified, and the grout fails to exude from the liquid outlet pipe 15 due to a blockage. The first rubber tube 1501 of the liquid outlet pipe 15 with the first water-stop clamp 16. The first peristaltic pump 2 is turned off to end the grouting.

The device for preparing the solidified cohesionless soil specimen for the triaxial test is operated as follows.

The second hoop 10 is configured to tightly combine the circumferential grouting cylinder 9 into a whole, and the PMMA pipe 8 is configured to tightly combine the first hoop 11 into a whole. When the second glass stopper 13 is inserted into the bottom of the PMMA pipe 8, until the bottom of the PMMA pipe 8 fits the top of the third lateral convex disc of the third cylinder 1301 in the second glass stopper 13, the top end of the second glass stopper 13 coincides with the zero-scale line of the graduation scale 801 on the side wall of the PMMA pipe 8. The liquid outlet pipe 15 is inserted from the second glass stopper 13 to the junction of the second glass stopper 13 and the cotton filter 1307, and two branch pipes of the end of the second glass stopper 13 close to the return pipe 12 are inserted from the second glass stopper 13 into the circumferential space 20. The circumferential grouting cylinder 9 is inserted into the circular slot where the second glass stopper 13 fits the circumferential grouting cylinder 9, until the position of the circumferential grouting cylinder 9 is fixed by a bottom of the circular slot.

The soil specimen to be solidified is put into the circumferential grouting cylinder 9, followed by the compaction or the static pressure according to relevant specifications until the required height is reached. The second electrode rod 14 extends into the specimen in the circumferential grouting cylinder 9 through the second glass stopper 13. The first glass stopper 7 is installed at the top of the PMMA pipe 8, and the circumferential grouting cylinder 9 is inserted into the slot bottom of the circular slot of the first glass stopper 7. The second cylinder 702 is moved to make its bottom surface contacts the top end of the specimen. The bolt 704 is configured to be rotated to fix the position of the second cylinder 702 relative to the first cylinder 701. The second vessel 18 is arranged directly under the liquid outlet pipe 15 to prepare for grouting.

The specific process of the grouting is described as follows.

The first water-stop clamp 16 is removed and the second water-stop clamp 17 clamps the second rubber tube 1201 on the return pipe 12 to prevent the grout from flowing through the return pipe 12. The first peristaltic pump 2 is turned on, and the second peristaltic pump 19 is turned off. After the grouting is performed for 3 hours, the DC power supply 6 is turned on for electrochemical grouting. And the current direction is changed every hour (If the grout needs to be replaced during the grouting process, the first peristaltic pump 2 and the DC power supply 6 are turned off, followed by removing the second water-stop clamp 17, and turning on the second peristaltic pump 19, until the grout returns to the storage vessel of grout, then the second peristaltic pump is turned off, and the second water-stop clamp is installed, then restart first peristaltic pump 2 to continue grouting, after replacing the grout). When the liquid outlet pipe 15 has no grout flowing out, and the grouting through each of the plurality of grouting holes 901 cannot be continued due to the blockage, the grouting ends. At this time, the first peristaltic pump is turned off and the first water-stop clamp 16 clamps of the first rubber tube 1501 at the bottom end of the liquid outlet pipe 15. The second water-stop clamp 17 is removed and the second peristaltic pump 19 is turned on, then the second peristaltic pump 19 is turned off until all the grout between the PMMA pipe 8 and the circumferential grouting cylinder 9 is pumped into the first vessel 1.

After the grouting is completed, the grouting pipe 3 is pulled out. The first hoop 11 is released after standing for a specified time. The first half pipe 802 and the second half pipe 803 of the PMMA pipe 8 is opened, and the third half pipe 903 and the fourth half pipe 904 of the circumferential grouting pipe 9 is opened to take out the bonded solidified specimen, and maintain it to a specified age. The specimen is put in the pressure chamber for the dynamic and static triaxial test. In this embodiment, both of the PMMA pipe 8 and the circumferential grouting cylinder 9 have a two-piece structure. The specimen can be removed under an interference-free condition, so as to prevent the specimen from damaging when the specimen is removed The above embodiments are only used to illustrate the objectives, technical solutions, and beneficial effects of this disclosure, and are not intended to limit the present disclosure. It should be understood that any replacements, changes and improvements made by those skilled in the art without departing from the spirit of this application should fall within the scope of this application defined by the appended claims.

What is claimed is:
1. A device for preparing a solidified cohesionless soil specimen for a triaxial test, comprising:
   a first vessel configured to accommodate a grout;
   a first peristaltic pump;
   a grouting pipe;
   a first branch pipe;
   a second branch pipe;
   a third branch pipe;
   a flow control valve;
   a first electrode rod;
   a direct-current (DC) power supply;
   a first glass stopper;
   a polymethyl methacrylate (PMMA) pipe;
   a circumferential grouting cylinder;
   a plurality of grouting holes;
   a first hoop;
   a second hoop;
   a return pipe;
   a second rubber tube;
   a second glass stopper;
   a cotton filter;
   a second electrode rod;
   a liquid outlet pipe;
   a first rubber tube;
   a first water-stop clamp;
   a second water-stop clamp;
   a second vessel for collecting an exudate;
   a second peristaltic pump; and
   a circumferential space;
   wherein, the first vessel is used to store the grout;
   the PMMA pipe is of a two-piece structure; the first hoop is sleevedly provided on an outer side wall of the PMMA pipe; and both of two ends of the PMMA pipe are open; a top opening of the PMMA pipe is provided with a first glass stopper, and a bottom opening of the PMMA pipe is provided with a second glass stopper;
   the circumferential grouting cylinder has a two-piece structure; the second hoop is sleevedly provided on an outer side wall of the circumferential grouting cylinder; the plurality of grouting holes are evenly provided on a side wall of the circumferential grouting cylinder; the circumferential grouting cylinder is arranged in the PMMA pipe, and the circumferential grouting cylinder and the PMMA pipe are arranged coaxially; the first glass stopper abuts against a top end of the circumferential grouting cylinder, and the second glass stopper abuts against a bottom end of the circumferential grouting cylinder; the circumferential space is formed between the circumferential grouting cylinder and the PMMA pipe, and a soil specimen to be solidified is prepared into the solidified cohesionless soil specimen in the circumferential grouting cylinder; a first end of the grouting pipe is connected to the first vessel, and a second end of the grouting pipe is provided with the first branch pipe, the second branch pipe, and the third branch pipe; the first branch pipe and the third branch pipe pass through the first glass stopper to partially extend into the circumferential space; the second branch pipe passes through the first glass stopper to be inserted into the soil specimen to be solidified in the circumferential grouting cylinder; the first peristaltic pump is arranged at the first end of the grouting pipe; the first peristaltic pump is configured to drive the grout in the first vessel to pass through the first end of the grouting pipe, and the first branch pipe and the third branch pipe at the second end of the grouting pipe in sequence to be injected into the soil specimen to be solidified in the circumferential space, and then to be injected into the soil specimen to be solidified in the circumferential grouting cylinder through the plurality of grouting holes; and the first peristaltic pump is also configured to drive the grout in the first vessel to pass through the first end of the grouting pipe, and the second branch pipe arranged at the second end of the grouting pipe in sequence to be injected into the soil specimen to be solidified in the circumferential grouting cylinder; the second electrode rod passes through the second glass stopper facing the soil specimen to be solidified is provided with the cotton filter; one end of the liquid outlet pipe passes through the second glass stopper to extend to a bottom of the cotton filter, and the other end of the liquid outlet pipe is arranged near an flow inlet of the second vessel; the exudate exuding from the circumferential grouting cylinder is configured to flow through the liquid outlet pipe and the inlet of the second vessel in sequence to be injected into the second vessel; one end of the return pipe extends into the circumferential space through the second glass stopper, and the other end of the return pipe is arranged near an inlet of the first vessel; the second peristaltic pump is configured to drive the grout in the circumferential space to return to the first vessel through the return pipe; one end of the first electrode rod extends into the soil specimen to be solidified in the circumferential grouting cylinder through the first glass stopper, and the other end of the first electrode rod is connected to a positive electrode of the DC power supply; an end of the second electrode rod away from the second glass stopper is connected to a negative electrode of the DC power supply; a combination of the DC power supply, the second electrode rod, and the first electrode rod is configured to enable an electrochemical grouting, so as to promote a flow diffusion of the grout in the circumferential grouting cylinder;

the first peristaltic pump and the second peristaltic pump both have an adjustable output power; the first rubber tube is sleevedly provided at the end of the liquid outlet pipe arranged near the inlet of the second vessel; the first water-stop clamp is arranged on the first rubber tube; the first water-stop clamp is configured to clamp or release the first rubber tube, so as to make the first rubber tube unblocked or blocked, thereby making the liquid outlet pipe unblocked or blocked; the second rubber tube is sleevedly provided on a middle of the return pipe, and the second water-stop clamp is arranged on the second rubber tube; the second water-stop clamp is configured to clamp or release the second rubber tube, so as to make the second rubber tube blocked or unblocked, thereby making the return pipe blocked or unblocked; and the flow control valve is arranged on the second branch pipe; the flow control valve is configured to control a flow rate of the grout in the second branch pipe, so as to achieve independent control of the flow rate of the grout in the second branch pipe.

2. The device of claim 1, wherein an inner diameter of the PMMA pipe is 79.1 mm; an inner diameter of the circumferential grouting cylinder is 39.1 mm or 38 mm; a diameter of each of the plurality of grouting holes is 0.075 mm, and a spacing between centers of each of the plurality of adjacent two grouting holes is 1 mm; and a side wall of the PMMA pipe is provided with a graduation scale of a height of at least 100 mm.

3. The device of claim 1, wherein the flow control valve is configured to control the flow rate of the grout in the second branch pipe, such that the flow rate of the grout in the second branch pipe is less than a flow rate of the grout in the first branch pipe and the third branch pipe.

4. The device of claim 1, wherein the first glass stopper comprises:
a first cylinder;
a second cylinder;
a sleeve; and
a bolt;
wherein the first cylinder is larger than the second cylinder; a side wall of the second cylinder fits an inner wall of the circumferential grouting cylinder; the first cylinder and the second cylinder are coaxially connected; the second cylinder is configured to move up and down relative to the first cylinder, to adjust a fitting length between the second cylinder and the circumferential grouting cylinder; the sleeve is fixedly connected to a top of the first cylinder; the bolt is penetratedly provided on the sleeve and is configured to abut against the second cylinder; the bolt is configured to be rotated to be close to or away from the second cylinder, such that the bolt abuts against the second cylinder or releases the second cylinder, thereby realizing locking and unlocking of a height of the second cylinder relative to the first cylinder; the first glass stopper is provided with a first through hole, a second through hole, a third through hole, and a fourth through hole; the first branch pipe is inserted into the first glass stopper through the first through hole; and the third branch pipe is inserted into the first glass stopper through the fourth through hole; the second branch pipe is inserted into the first glass stopper through the second through hole; the first electrode rod is inserted into the first glass stopper through the third through hole; an inner wall of each of the first through hole, the second through hole, the third through hole and the fourth through hole is pasted with a first anti-slip film to fix the components inserted into the first glass stopper.

5. The device of claim 1, wherein the second glass stopper comprises a first cylinder and a second cylinder; the first cylinder is larger than the second cylinder; the first cylinder and the second cylinder are arranged coaxially; the cotton filter is attached to an end of the second glass stopper in contact with the soil specimen to be solidified to prevent the soil specimen to be solidified from leaking; the liquid outlet pipe and the return pipe do not pass through the cotton filter, while the second electrode rod passes through the cotton filter; the second glass stopper is provided with a first through hole, a second through hole, a third through hole and a fourth through hole; one end of the return pipe is arranged near the inlet of the first vessel, and the other end of the return pipe is provided with a fourth branch pipe and a fifth branch pipe; the fourth branch pipe is inserted into the second glass stopper through the first through hole, and the fifth branch pipe is inserted into the second glass stopper through the fourth through hole; the liquid outlet pipe passes through the second glass stopper through the second through hole to extend to a bottom of the cotton filter; and the second electrode rod passes through the second glass stopper through the third through hole to be inserted into the soil specimen to be solidified.

6. The device of claim 1, wherein a gauze is attached to the side wall of the circumferential grouting cylinder to prevent the soil specimen to be solidified from leaking out of the circumferential grouting cylinder.

7. The device of claim 1, wherein the first electrode rod, the second electrode rod and the DC power supply together establish a complete electric field inside the soil specimen to be solidified to realize the electrochemical grouting; the electric field is configured to control a flow of the grout with different charges in the soil specimen to be solidified, and is configured to switch the positive electrode and the negative electrode of the DC power supply to change a current direction, so as to change a flow direction of the grout.

8. The device of claim 1, wherein the second vessel is configured to collect the grout exuded from the circumferential grouting cylinder through the liquid outlet pipe.

9. The device of claim 1, wherein a distance between a bottom end of the first glass stopper and a top end of the second glass stopper is 100 mm; the bottom end of the first glass stopper is aligned with a 100 mm scale line of the graduation scale on the side wall of the PMMA pipe; the top end of the second glass stopper is aligned with a 0 mm scale line of the graduation scale on the side wall of the PMMA pipe.

10. A method for preparing a solidified cohesionless soil specimen for triaxial test using the device of claim 1, comprising:

opening the first glass stopper, and putting a soil specimen to be solidified into the circumferential grouting cylinder followed by layered compaction to form a cylindrical specimen with a diameter of 39.1 mm or 38 mm and a height of 80 mm-100 mm; and inserting the first glass stopper into the top opening of the PMMA pipe;

turning on the first peristaltic pump to drive the grout in the first vessel to be injected into the circumferential space through the first end of the grouting pipe and the first branch pipe and/or the third branch pipe at the second end of the grouting pipe in sequence; laterally injecting the grout into the specimen to be solidified in the circumferential grouting cylinder through the plurality of grouting holes of the circumferential grouting cylinder to perform circumferential grouting; and simultaneously driving, by the first peristaltic pump, the grout in the first vessel to pass through the first end of the grouting pipe and the second branch pipe at the second end of the grouting pipe in sequence to be injected into the soil specimen to be solidified in the circumferential grouting cylinder to perform a vertical grouting inside the soil specimen to be solidified;

after the grouting is performed for 3 hours, turning on the DC power supply to allow the DC power supply to cooperate with the second electrode rod and the first electrode rod to perform an electrochemical grouting, so as to allow the grout to flow and diffuse in the circumferential grouting cylinder until a desired solidified triaxial test specimen is obtained; wherein the grouting of the device comprises processes of grouting, standing and re-grouting; the grout is a single or mixed grout;

turning off the first peristaltic pump to stop the grouting after completing an injection of the grout, wherein during the grouting process, the second rubber tube of the return pipe is clamped by the second water-stop clamp to block the return pipe, and the first water-stop clamp is removed from the liquid outlet pipe to make the liquid outlet pipe unblocked; the first water-stop clamp clamps the first rubber tube of the liquid outlet pipe, after the grouting is completed, the first rubber tube of the liquid outlet pipe is clamped by the first water-stop clamp to block the liquid outlet pipe, and the second peristaltic pump is turned on to pump the grout remaining in the PMMA pipe into the first vessel through the return pipe; and after standing for a preset period of time, replacing the grout with another grout or directly repeating the above steps to perform re-grouting.

11. The method of claim 10, wherein the grouting is ended through steps of:

turning on the first peristaltic pump and removing the first water-stop clamp, when the grout is blocked from being injected into the soil specimen to be solidified, and the grout fails to exude from the liquid outlet pipe due to a blockage; clamping the first rubber tube of liquid outlet pipe with the first water-stop clamp; and turning off the first peristaltic pump to end the grouting.

* * * * *